(12) United States Patent
Deminiere et al.

(10) Patent No.: US 8,933,126 B2
(45) Date of Patent: Jan. 13, 2015

(54) METHODS OF ADMINISTERING A MIXTURE OF FATTY ACIDS FOR THE TREATMENT OF NON-HUMAN MAMMALS

(75) Inventors: Benedicte Deminiere, Pomerol (FR); Sandrine Lacoste, Carignan (FR); Marie-Laure Loubiere, Bordeaux (FR)

(73) Assignee: Ceva Sante Animale, Libourne, Cedex (FR)

( * ) Notice: Subject to any disclaimer, the term of this patent is extended or adjusted under 35 U.S.C. 154(b) by 409 days.

(21) Appl. No.: 12/995,216

(22) PCT Filed: May 29, 2009

(86) PCT No.: PCT/EP2009/056679
§ 371 (c)(1),
(2), (4) Date: Nov. 30, 2010

(87) PCT Pub. No.: WO2009/144321
PCT Pub. Date: Dec. 3, 2009

(65) Prior Publication Data
US 2011/0077301 A1    Mar. 31, 2011

(30) Foreign Application Priority Data

May 30, 2008  (FR) ..................................... 08 02989

(51) Int. Cl.
*A61K 31/20*    (2006.01)
*A61K 9/00*     (2006.01)

(52) U.S. Cl.
CPC .................. *A61K 9/007* (2013.01); *A61K 31/20* (2013.01)
USPC ............ 514/560; 514/549; 514/552; 514/558

(58) Field of Classification Search
None
See application file for complete search history.

(56) References Cited

U.S. PATENT DOCUMENTS

| 4,804,821 | A   | * | 2/1989 | Glucksman | ................... 392/390 |
| 5,805,768 | A   | * | 9/1998 | Schwartz et al. | ............. 392/390 |
| 6,384,252 | B1  |   | 5/2002 | Pageat | |
| 6,920,282 | B2  | * | 7/2005 | He et al. | ........................ 392/392 |
| 7,252,805 | B2  | * | 8/2007 | Hart et al. | ..................... 422/125 |

FOREIGN PATENT DOCUMENTS

| GB | 2071497 | * | 9/1981 | ................ A61L 9/03 |
| GB | 2252907 | * | 8/1992 | ................ A61L 9/03 |

OTHER PUBLICATIONS

PCT International Search Report, Sep. 28, 2009, for Ceva Sante Animale et al., Int'l App'l No. PCT/EP2009/056679, filed May 29, 2009.
PCT Written Opinion of the International Searching Authority, Sep. 28, 2009, for Ceva Sante Animale et al., Int'l App'l No. PCT/EP2009/056679, filed May 29, 2009.
PCT International Preliminary Report on Patentability, Dec. 6, 2010, for Ceva Sante Animale et al., Int'l App'l No. PCT/EP2009/056679, filed May 29, 2009.
Tod et al., 2005, "Efficacy of Dog Appeasing Pheromone in Reducing Stress and Fear Related Behaviour in Shelter Dogs", Applied Animal Behaviour Science, vol. 93: 295-308.

* cited by examiner

*Primary Examiner* — Yate K Cutliff
(74) *Attorney, Agent, or Firm* — Saliwanchik, Lloyd & Eisenschenk

(57) ABSTRACT

Mixture of fatty acids, their derivatives, ester or methyl ester derivates thereof, which may be administered to non-human mammals by diffusion in to ambient air during at least seven consecutive days, with a rapid kinetic of diffusion during the first three days of administration.

9 Claims, 4 Drawing Sheets

Figure 1:
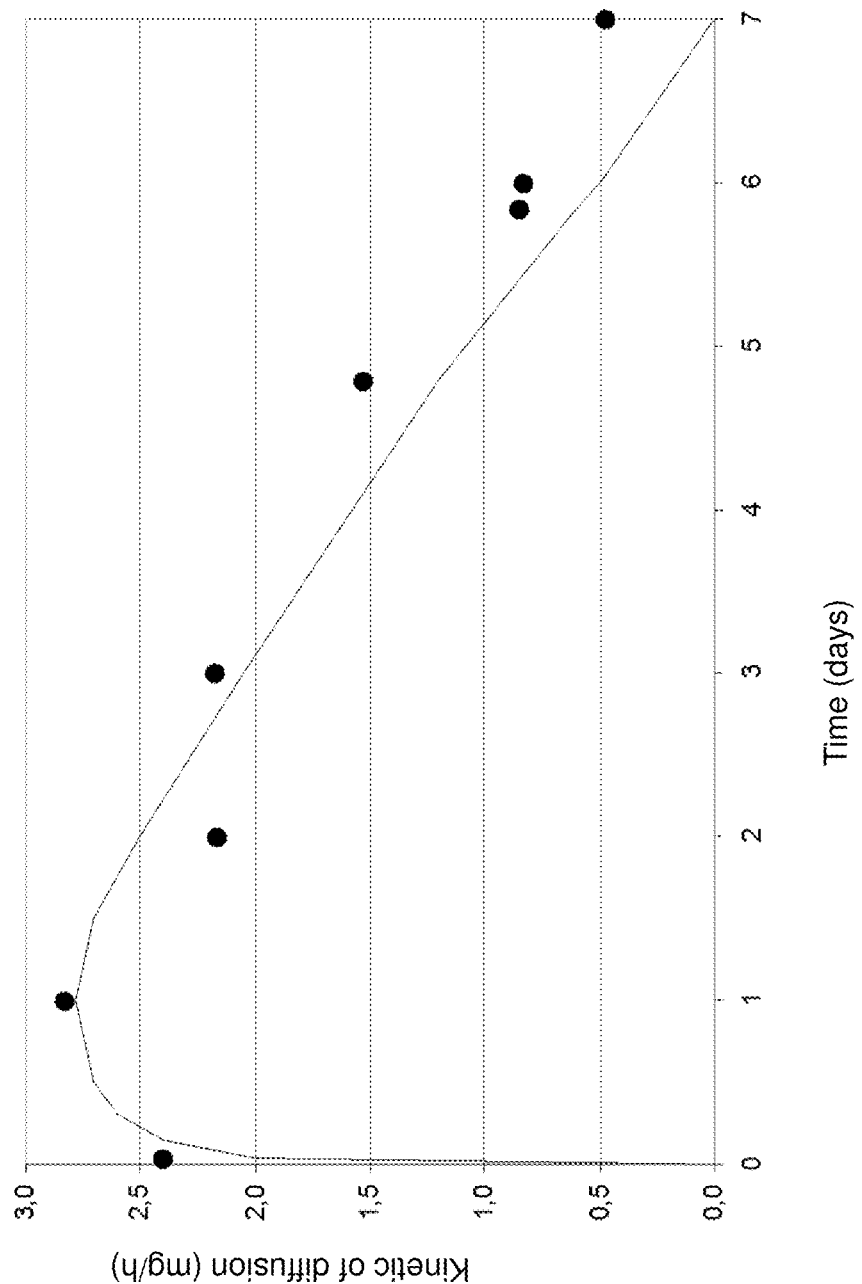

METHODS OF ADMINISTERING A MIXTURE OF FATTY ACIDS FOR THE TREATMENT OF NON-HUMAN MAMMALS

This application is the National Stage of Int'l App'l No. PCT/EP2009/056679, filed May 29, 2009, which claims priority of French Application No. 0802989, filed May 30, 2008. The entire contents and disclosures of the preceding applications are incorporated by reference into this application.

The present invention relates to a mixture of pure fatty acids and their derivatives which may be administered to non-human mammals by air diffusion. This allows for an effective prevention of territorial marking or reduction of stress, distress expressed in the form of destructions, loud and noisy behavior, dirtiness or aggressiveness.

Similar to humans, stress or anxiety in domestic animals such as cats and dogs can translate into drastic physiological and metabolic changes, changes to the neuroendocrine system and to the immune system, as well as behavioral changes. These reactions to stress and anxiety occur frequently due to sudden changes to the immediate environment of these animals, usually because of transport, moving to unfamiliar places, inclusion of these animals into new families or in the presence of other unfamiliar animals or people.

It is common practice to use psychotropic and neuroleptic medicines in veterinary medicine, it is even more common to use tranquilizers to try and reduce the symptoms associated with stress.

Fatty acid compositions having an appeasing and relaxing effect on some mammals have also been used to fight animal anxiety due to stress. To this regard, one can cite appeasing products for cats. These consist essentially of diluted solutions or fatty acid emulsions from the pheromones of cats, for example in the form of sprays. These aerosol compositions, amongst others have been described in the U.S. Pat. No. 5,709,863. These aerosols consist of pheromone fatty acids, solvents and a vegetable extract of *Valeriana* aiming to attract cats to a place in the room where the mixture is sprayed.

Similar compositions are also described for dogs, for example in the U.S. Pat. No. 6,384,252. They are made up of a base of apaisine, a pheromone secreted from the skin around the mammary sebaceous glands of the suckling female dogs. Appeasing fatty acid compositions for pigs derived from the secretions of mammary glands also exist. These compositions are described in the U.S. Pat. No. 6,077,867.

These different compositions however generally in the form of emulsions or micro-emulsions as described in the U.S. Pat. No. 6,500,862. These emulsions or micro-emulsions consist of fatty acids, surfactants preferably anionic or non-ionic and up to 30% of co-surfactants such as linear or branched alcohols in $C_1$-$C_{12}$.

When such emulsions or microemulsions are used, it thus required repeating the spraying of the fatty acids in different parts of the room until stress and anxiety related behavior is reduced. Alternatively, electrical diffusion device of liquids containing the pheromones has been used. Volatile fatty acids are then in the form of solution in the solvents so as to assure that their stability in the electric diffuser at high temperatures. These products generally diffuse fatty acids in the ambient air in very small quantities with slow and continuous kinetic diffusions lasting for long periods of time such as a month approximately.

This present invention relates to a mixture of pure fatty acids and their administration with a rapid kinetic during the first few days, resulting into a reduction of the stress and anxiety of non-human mammals. In contrast with conventional relaxing products, the mixtures according to the present invention comprise pure fatty acids and/or derivatives thereof, which are not in the forms of dilutions or emulsions in solvents or in surfactants. These mixtures maintain a good stability even when they are heated to approximately 120° C. to allow their diffusion in the air. In addition, they are administered to non-human mammals by diffusion in the air with rapid kinetics of diffusion during the first three days and they are administered during short periods of time: few days. More precisely, they are administered with kinetics of diffusion which are twice greater than the conventional kinetics of diffusion during the first three days. The kinetics are then decreasing in time, in contrast device having conventional kinetics of diffusion, such as recharged electric liquid, which are constant over time. Although the kinetics of diffusion and thus doses as administered to non-human mammals are very different from that of conventional products, the relaxing effects on the non-human mammals are very satisfactory and the general behavior of the treated non-human mammals is significantly improved. Therefore, the state of stress and anxiety observed in non-human mammals caused due to sudden and drastic changes to their immediate environment are significantly reduced.

The present invention relates to composition or a mixture comprising one or more fatty acids, as active ingredients, and/or ester or methyl ester derivatives thereof. The composition thus consists of a pure fraction or pure mixture of esters of fatty acids or derivatives of methyl ester which may be administered to non-human mammals through diffusion in to ambient air. The proportions of fatty acid, ester derivatives or methyl ester derivatives are approximately between 77 and 94%, preferably between 85 and 90% or equal to approximately 90%.

"Fatty acids" means according to the invention hydrocarbon chain with monocarboxylic or dicarboxylic acids, saturated or unsaturated, linear or branched, and active, and capable of inducing behavior changes in non-human mammals. These fatty acids generally have C4-C22. They are chosen among oleic acid, palmitic acid, azelaic acid, pimelic acid, capric acid, myristic acid, palmitoleic acid, linoleic acid, stearic acid, arachidonic acid, n-butyric acid, isobutyric acid, α-methylbutyric acid, capric acid, pivalic acid, γ-linoleic acid, eicosapentanoic acid, pentadecanonic acid, tridecanoic acid or docosahexanoic acid.

"Derivatives of fatty acids" means all active, volatile derivatives of fatty acids. Preferably, the derivatives are in ester or methyl ester forms.

The mixtures comprise a pure fraction of at least one fatty acid such as oleic acid, derivatives of oleic acid, ester or methyl ester derivative thereof. The mixtures may also comprise without limitations, compositions of fatty acids that are suitable to reduce stress and anxiety behaviors of non-human mammals, derivatives thereof, esters or methyl ester derivatives thereof. By way of examples, we can cite fatty acid mixtures, or their derivatives, ester or methyl ester derivatives such as:

a mixture of oleic and palmitic acid;
a mixture of oleic and n-buytric acid;
a mixture of oleic acid, palmitic acid and linoleic acid;
a mixture of oleic acid, palmitic acid, linoleic acid and palmitoleic acid;
a mixture of capric acid, lauric acid, myristic acid, palmitoleic acid, palmitic acid, linoleic acid and oleic acid;
a mixture of oleic acid, palmitic acid, linoleic acid, myristic acid;
a mixture of oleic acid, palmitic acid, linoleic acid, lauric acid and myristic acid a mixture of oleic acid, palmitic acid, linoleic acid, myristic acid and pentadecanonic acid;

a mixture of oleic acid, palmitic acid, linoleic acid, myristic acid, pentadecanonic acid and stearic acid;

a mixture of oleic acid, palmitic acid, linoleic acid, myristic acid, lauric acid and pentadecanonic acid;

a mixture of lauric acid, myristic acid, pentadecanonic, palmitic acid, stearic acid, oleic acid, linoleic acid; or a mixture of oleic acid, azelaic acid, pimelic acid and palmitic acid.

The mixtures may comprise the above-mentioned fatty acids in appropriate proportions which are well known to any skilled person. By way of example, the mixtures can contain:

about 55-65% of oleic acid and 45-35% of palmitic acid, their derivatives, and its ester or methyl ester derivatives;

about 45% of oleic acid, 16% of azelaic acid, 18% of pimelic acid, and 21% of palmitic acid, their derivatives, ester or methyl ester derivatives thereof;

about 30% of palmitic acid, 30% of oleic acid, and 40% linoleic acid, their derivatives, ester and methyl ester derivatives thereof; or about 30% of palmitic acid, 40% of linoleic acid, 10% acid palmitoleic and 20% of oleic acid, their derivatives, ester and methyl ester derivatives thereof.

According to the first embodiment of the present invention, the fatty acid mixture comprises a mixture of appeasing fatty acids for cats. Preferably, this mixture comprises at least a therapeutically effective amount of active fatty acids, derivatives thereof, ester or methyl ester derivatives thereof, and chosen among oleic acid, azelaic acid, pimelic acid and palmitic acid. The pure mixture of fatty acids comprises at least between about 45-60% oleic acid, 6-10% of azelaic acid, 8-12% of pimelic acid, and 13-18% of palmitic acid. In the case where ester and methyl ester forms are used, the pure mixture comprises between about 45-65% methyl oleate, between about 6-10% dimethyl azelate, between about 8-12% of dimethyl pimelate, and between about 13-18% of methyl palmitate. Preferably, the pure mixture of esters of fatty acids consist approximately 47-51% of methyl oleate, approximately 7-9% of azelate of dimethyl, between 9-11% of dimethyl pimilate and approximately 14-16% of methyl palmitate.

According to a second embodiment of the invention, the mixture comprises a mixture of fatty acids that are appeasing for dogs. Preferably, this mixture comprises a therapeutically effective amount of fatty acids, their derivatives, ester or methyl ester derivatives thereof. These are preferably chosen among lauric acid, myristic acid, pentadecanoic acid, palmitic acid, stearic acid, oleic acid and linoleic acid. By way of example, a pure mixture of ester fatty acids for dogs comprises about 35% of methyl oleate, about 2% dimethyl laurate, about 13% methyl stearate, about 21 methyl linoleate, about 5% methyl myristate, about 4% methyl pentadecanoate, and about 20% methyl palmitate.

According to a third embodiment, the mixture comprises a mixture of pure fatty acids capable of reducing the stress and aggressiveness of pigs, comprising about 45% oleic acid, 16% azelaic acid, 18% pimelic acid, and 21% palmitic acid, their derivatives, ester or methyl ester derivatives thereof. The mixture can thus comprise about 30% palmitic acid, 30% oleic acid, and 40% linoleic acid, their derivatives, ester or methyl ester derivatives thereof; or about about 30% palmitic acid, 40% linoleic acid, and 10% palmitoleic acid, and 20% oleic acid, their derivatives, ester or methyl ester derivatives thereof. Other fatty acid mixtures are also known for their relaxing properties in pigs and comprise about 3% capric acid, 8% lauric acid, and 9% myristic acid, 10% palmitoleic acid, 20% palmitic acid, 30% linoleic acid, and 20% oleic acid, their derivatives, ester or methyl ester derivatives thereof The fatty acid mixtures, their derivatives, ester or methyl ester derivatives thereof remain pure. They are devoid of solvent, excipients, vegetable extracts, such as vegetable extracts of *Valeriana*, or even aqueous phase. They only comprise one oily phase corresponding to a pure fraction of fatty acids, their derivatives, ester or methyl ester derivatives thereof and are not in the form of emulsions or micro-emulsions. They are present in the form of oily and liquid phases depending of the temperature and may be heated by any appropriate means so as to obtain a diffusion of fatty acids and their derivatives, ester or methyl ester derivatives thereof in the air.

Thereby, the fatty acid mixtures according to the invention, may be administered to non-human mammals by diffusion in the ambient air, according to rapid diffusion kinetics during short periods of time, that are better or superior to existing systems. The administration of non-human mammals takes places by heating and by diffusion of the mixture of fatty acids in the ambient air during at least six to seven consecutive days with a kinetic peak of diffusion that is higher than 2 mg/hour during the first three days of the administration by diffusion. The kinetic peak of diffusion is preferably between 2-3 mg/h, or between 2.5 and 3 mg/h during these three days.

The preferred profiles of the administration kinetics of the compositions according to this present invention which have been shown as having beneficial appeasing effects to non-human treated mammals are as follows:

(i) higher than about 1.5 mg/h during the first five days,
(ii) then about 0.58 to 1 mg/h on the sixth day, and then
(iii) lesser than about 0.5 mg/h during the seventh day.

or (i) higher than about 2 mg/h during the first three days, then
(ii) about 1.5 to 2 mg/h during the fourth day,
(iii) about 1 mg/h during the fifth and sixth day, and then finally
(iv) lesser than 0.5 mg/h during the seventh day.

During the administration of the mixture of the fatty acids according to these particular kinetics, the fatty acids or their derivatives, ester or methyl ester derivatives thereof are diffused in the air according to the proportions determined in the course of the treatment with the objective of achieving the appeasing or relaxing effect on non-human mammals. The amounts of the fatty acids, their derivatives, ester or methyl ester derivatives thereof, administered by air diffusion are as follows: 200 mg of fatty acids or their derivatives, ester or methyl ester derivatives thereof, are diffused in to air during the first three days after the start of the diffusion, and 70 mg are diffused in the air between the third and sixth day of diffusion, the total amount of fatty acids or their derivatives, ester or methyl ester derivatives thereof, diffused during the seven consecutive days being 240 mg.

The administration is done by inhaling by non-human mammals, of the compositions of fatty acids, their derivatives, ester or methyl ester derivatives thereof, which are diffused in the ambient air around the non-human mammal's habitat.

These fatty acid mixtures, their derivatives, ester or methyl ester derivatives thereof, are particularly effective in preventing territorial urinary marking and/or in reducing anxiety or stress related symptoms, and/or in familiarizing the animals with a new environment, and/or in preventing noisy outbursts, soiling, destructions, stamping in the territories or aggressiveness. The fatty acid mixtures are equally useful for the prevention and/or treatment of recurrent idiopathic cystitis, notably in stressed or anxious felines.

The administration of the mixtures may take place over short periods of time of at least six to seven consecutive days. It can be renewed if necessary in order to be adapted to stress and anxiety behaviors of the non-human mammals, according to the severity of the pathology, or the weight of the animal.

The present invention also relates to the use of fatty acids, their derivatives, ester or methyl ester derivatives thereof, for the preparation of a composition for treating stress and anxiety in non-human mammals, and/or for preventing urinary marking, noisy outbursts and/or to familiarize the non-human mammals with a new environment, and/or to prevent stamping or territorial destruction. It also relates to a method of preventing and/or reducing stress or anxiety, noisy outbursts, or a method aiming to prevent stampings or territorial destructions which comprises administering fatty acids their derivatives, ester or methyl ester derivatives thereof, according to kinetics of administration as described above.

The method according to the present invention allows to improve, in some cases, acquaintance of the non human mammals with a new environment, for example during transportation or when moving in a new place. The method according to the present invention also allows reducing recurrent idiopathic cystitis, notably in stressed or anxious felines.

"Non-human mammals" is intended to mean all animals with the exception of human, and it refers notably to domestic animals such as dogs and cats.

The novel modes of administration and dosages according to the present invention are particularly efficient on cats to a large extent, including all the members of the feline and feline family, domestic cats, and more commonly all races of cats. Indeed, cats display very specific symptoms of stress and anxiety, such as territorial urinary markings. This refers to some olfactory and instinctive behavior of cats, includes urinating or urine spraying in various places in order to mark its territory and therefore warn its eventual fellow creatures. These patterns of urination can increase or be accentuated during stress or anxiety. Cats can increase their urinary marking in reaction to stress, typically in such situations as moving, or in the presence of another animal, or with the arrival of a new baby. It is obvious that these urinary markings mainly represent important health issues.

The mixtures, uses and methods according to the present invention thus allow reducing the repetitive urinary markings of cats occurring in case of stress and or anxiety of non-human mammals due to circumstances or particular changes to their immediate environment. It also allows the improvement of the conditions for the non-human mammals to familiarize themselves with their new environment and or to prevent stamping and territorial destructions, and/or reduce noisy outbursts.

The beneficial effects can be measured by the reduction of the urinary markings and by the repeated physical contact or rubbing against new objects and people that surround them. On the whole, the mixture of fatty acids according to the present invention allows the improvement of behavior of the non-human mammals in general vis-à-vis their environment and the people present in that environment, with a notable reduction of stress, anxiety, urinary marking and or noisy outbursts, as well as behavior that is non aggressive and more relaxed and more affectionate, especially with their owners.

The mixture of fatty acids, their derivatives, ester or methyl ester derivatives thereof, according to the invention may be diffused in the ambient air by any means or devices of diffusion by heat in order to obtain the kinetics of administration as described above. The heating devices suitable to permit a diffusion of fatty acids into the ambient air according to the invention may be for examples, sources of heat combustion such as candle flames, a benzene beak, a gas stove, slow burning wood, or a source of heat by contact such as electric resistance, a bath of water or oil, or even a solar heat source such as an optic device which focuses sun rays. Preferably, the heat source chosen allows a temperature between 100 and 140° C. during seven days.

In ambient temperatures, the fatty acid mixtures can present themselves under a liquid form or under a solid form, which is a function of the length and the structure of the carbon chain.

When the fatty acid mixtures are presented in a solid form, they may be placed in proximity to a heat source described above. When the fatty acid mixtures are in a liquid oily form, they are absorbed through a diffusion device, such as a porous support that is heated to ensure the diffusion of the mixtures described above. The support may thus allow the absorption of between 200 to 400 mg of pure fatty acid mixtures according to the invention. These porous supports are chosen according to their chemical nature in such a way that there is no chemical interaction, in particular no degradation of the fatty acid compositions described above. As examples of porous support capable of absorbing an effective quantity of pure fatty acids according to the present invention, one can cite polymer or synthetic matrices made with PVC for example, or latex, mineral, crystalline or amorphous matrices, which are for example made of ceramic or pumice stone, organic matrices for example made with wood, vegetable fibers such as cotton or bamboo fibers. The nature of the materials chosen, its porosity and affinity to the mixture to be diffused as well as its geometry and dimensions are set so as to accommodate 200 to 400 mg of fatty acids.

The porous supports may eventually be surrounded by a hermetic envelope having an opening that allows controlling the kinetic of evaporation. The envelope is chosen for its chemical compatibility with the fatty acids in contact with the internal film, its water tightness and its capacity to homogeneously conduct heat to fatty acids. By way of examples, the materials that constitute the envelop may be a plastic made of many layers of different kinds of polymers, or a metallic film, such as aluminum, or even a superimposition of layers of films of different kinds, such as plastic, organic films or metallic films.

Solid fatty acid mixtures or porous supports on which a significant quantity of oily mixture is absorbed may be placed in to devices appropriate to ensure the diffusion of heat and administration to the ambient air according to the kinetics of diffusion of the invention.

The present invention also relates to a kit or an administrative device for the diffusion of fatty acids, their derivatives, ester or methyl ester derivatives thereof, to non-human mammals permitting their diffusion in the air according to rapid kinetics of diffusion and during short durations of time of at least six to seven days with a kinetic peak of diffusion higher than 2 mg/h, or preferably between 2-3 mg/h, or between 2.5-3 mg/h during the first three days.

These devices may be in particular, electric devices for vaporizing or diffusion comprising solid support having a ceramic plate and a polymer matrix on which sufficient quantities of fatty acids, their derivatives, ester or methyl ester derivatives thereof, are applied in a way that the diffusion can take place according to the kinetics of this invention. These devices may be in the form of an electric pin fitted with a compartment consisting of the support ceramic plate that is suitable for heating and on which one can place a small plate impregnated with the composition of the fatty acids according to the invention. The device is made active by plugging to an electric source. The fraction of the fatty acids, their derivatives, ester or methyl ester derivatives thereof, is diffused under the effect of the heat through the openings in the compartments of the small plate. These are comparable to the ones used for diffusing anti mosquito repellents. They are preferably made of cellulose impregnated with a sufficient quantity of fatty acid compositions to allow for the diffusion of the fatty acids, their derivatives, ester or methyl ester derivatives thereof according to the kinetics of the invention. In addition, the small plate comprises neither solvent, nor any vegetable extracts of *Valeriana* or any other vegetable extract. Preferably, it is enveloped by a plastic film in order to adjust the kinetics of diffusion and to obtain the desired dose-appeasing effect on non-human mammals. Alternatively, this plastic envelope may be replaced by other appropriate envelopes such as the examples described below. Apart from the mixture of fatty acids, their derivatives, ester or methyl ester derivatives thereof, the plate may be impregnated with a pigment such as a yellow pigment or any other appropriate colors, and with an antioxidants. The proportions used for the fatty acid mixtures comprise between about 85 to 90%, or equal to 90%, and 1 to 10% of pigment and antioxidant, preferably between 5 to 7%, and equal to about almost 6%.

The present invention will be better understood in view of the Examples below and Figures.

Figure 2:
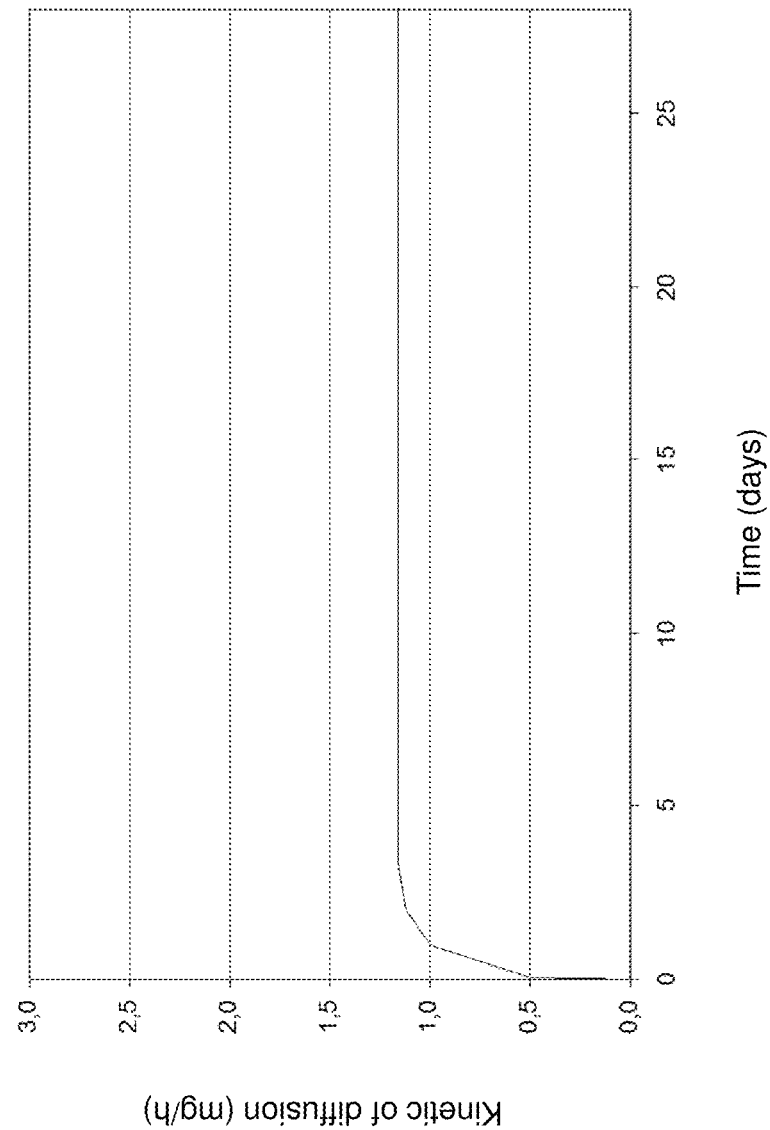
Figure 3:
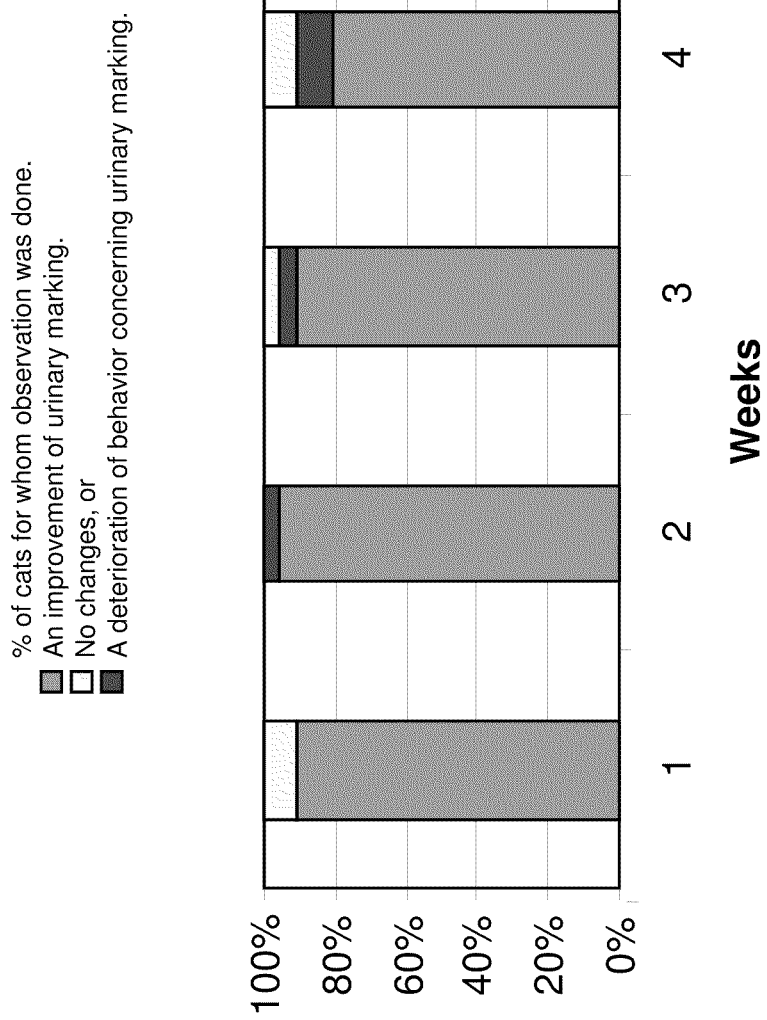
Figure 4:
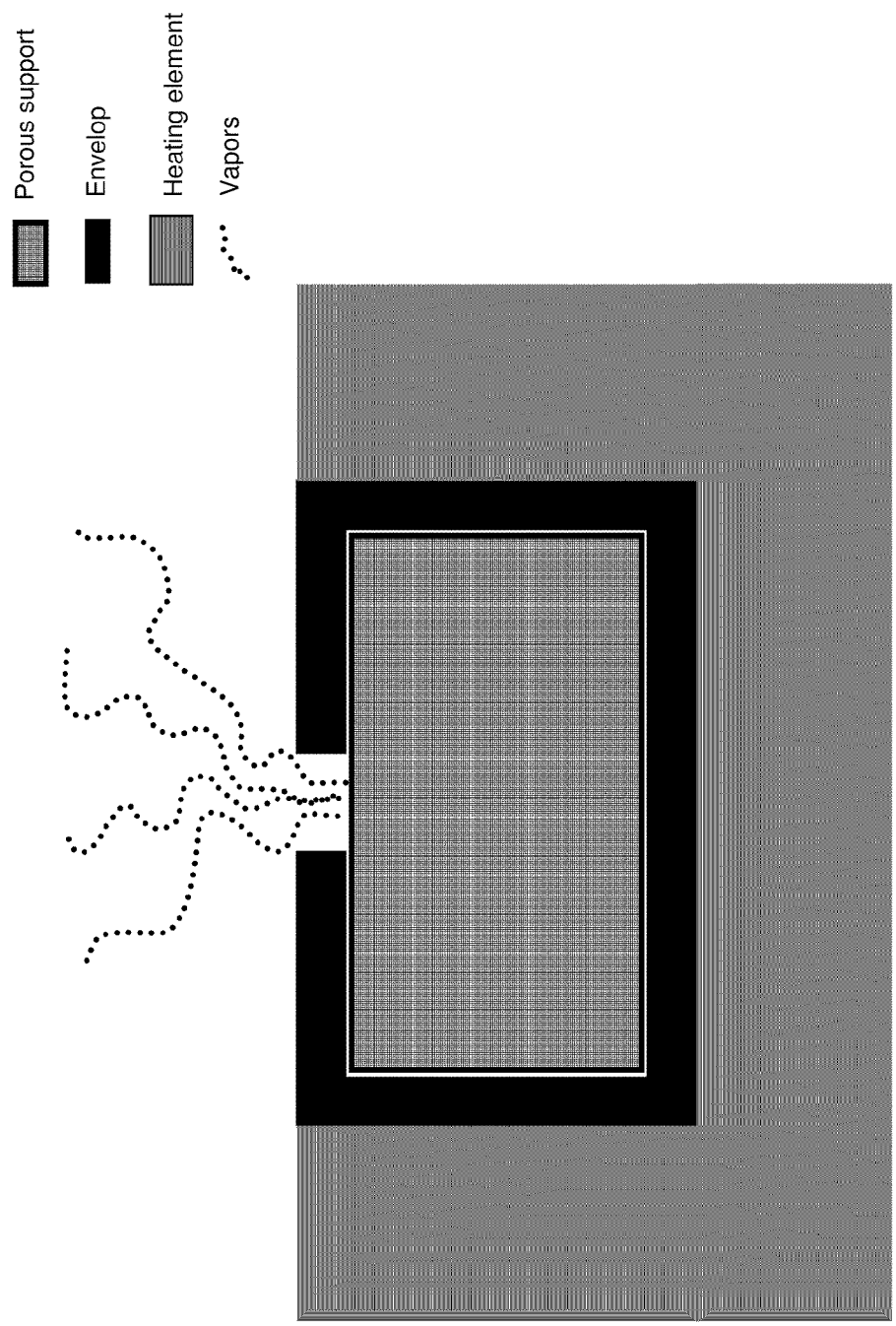

FIG. 1: Pattern of kinetic of diffusion according to the invention for the administration of the fatty acid mixtures to cats;

FIG. 2: Pattern of kinetic of diffusion of the fatty acids obtained through traditional devices;

FIG. 3: Histogram showing the improvement of the urinary markings of cats after the administration of the fatty acid mixtures obtained by using the kinetics of the present invention;

FIG. 4: Standard device such as an essential oil diffuser comprising a porous support which absorbs an effective amount of fatty acid mixtures according to the invention, the device being enveloped and placed within a heating element.

EXAMPLES

Example 1

Administration of Fatty Acid Mixtures to Cats Through Diffusion

A mixture of pure esters of fatty acids comprising approximately 48% of methyl oleate, about 8% of dimethyl azelate, approximately 10% of dimethyl pimelate, and approximately 15% of methyl palmitate were prepared. No solvent, vegetable extract such as vegetable extract of *Valeriana*, or any other vegetable extract were added to this mixture. A small disc of cellulose was impregnated with a mixture of pure esters, fatty acids and enveloped by a plastic film. The plate was thus impregnated, enveloped by a plastic film, was placed in to a diffusing device such a mosquito repellent device, and was connected to an electric source in order for the diffusion of the mixture to take place with the help of heat. Alternatively other plates were impregnated with 5% pigment and 6% antioxidant.

A test was conducted on 22 domestic cats having problems of urinary marking. Prior to being included in this study, the cats underwent a physiological examination and the behavioral history was established. It was also established that these cats had not received any particular treatments during the two months before the testing.

In the absence of any treatment, the number of urinary markings during a week was counted with the objective of quantifying the problem. The administration of the fatty acid mixtures was done through the diffusion according to the kinetics of the invention described before. The number of urinary markings was counted every week of the treatment. The treatment was renewed every week, during four consecutive weeks. The results of this study were gathered together in the FIG. 3 and showed a clear improvement of the urinary markings, which were reduced between 80 to 90%, very soon after the beginning of the treatment.

Example 2

Administration of Fatty Acid Mixtures by Diffusion to Dogs

A pure fatty acid ester mixture comprising approximately 35% methyl oleate, approximately 2% of dimethyl laurate, approximately 13% methyl stearate, approximately 21% of methyl linoleate, approximately 5% methyl myristate, approximately 4% of methyl pentadecanoate and approximately 20% methyl palmitate is prepared.

No solvent, vegetable extract such as vegetable extract of *Valeriana* or any other vegetable extract is added to this mixture.

A small disc of cellulose of 1.5 to 3 cm is impregnated with a pure mixture. The small plate is then enveloped with a plastic film, placed in a device such as a mosquito repellent device, and connected to an electric point in order for the diffusion of the mixture to take place with the help of heat. Alternatively, other discs are impregnated with 5% pigment and 6% antioxidant.

During a first study, the device is used for the young Labrador puppies (aged between 6 to 10 weeks) when they are newly adopted as they usually take a longer period of time to adapt themselves than the normal average time. 12 puppies participate in this test; 2 groups of six puppies each randomly chosen, each one receiving the mixture of pure fatty acid esters described above or a placebo (device with a plate impregnated with an inert substance). The inert substance used is the solvent that is used for conventional diffusions.

The treatment consists of using the device during two weeks, while renewing the impregnated plate after the first week of testing. The parameter of measure is the number of nights during which the owners of the puppies are awakened. To be precise, for this to be effective on 21 puppies, a median of 9 agitated nights is observed amongst the puppies receiving the placebo (pure solvent). The number of agitated nights amongst the puppies receiving the fatty acid ester mixtures according to the kinetics of diffusion of the present invention is compared to the number of agitated nights of the puppies receiving the inert substance (Placebo).

The acid mixture and the device are also tested in a veterinary clinic. The visit to the veterinarian is commonly viewed by dogs as a stressful event. An effective number of tests were done on 200 dogs.

The test consists of four phases. Each phase lasts a week and during each phase, 50 randomly chosen dogs visit the vet and their behavior is scored according to a scale of 1 to 6 in terms of the levels of stress. The score 1 corresponds to a dog that is completely relaxed and which lies down on the floor with all its limbs spread out. The score 6 corresponds to a state of stress that is very high and which can manifest itself in the form of aggressive behavior (the dog shows its teeth, lowers its ears, has its hair raised, grunts and growls when a stranger approaches) or by a marked state of shock (dog that is folded up by its own, that tries to hide under the furniture or behind its master, yelps with fear).

During the first week, the device comprising a mixture of pure fatty acids that are diffused according to the kinetics of the present invention is used, then alternatively, the inert solvent is used to study the placebo effect. A statistical analysis of stress manifestations is then created following the administration by diffusion of the appeasing acid mixture according to the kinetics of the invention.

Finally, a test is placed in the homes of the owners who come to consult the vet about the behavior problems of their pets. Included in the testing are also animals that show stress related behavior, notably: general anxiety or separation, fear of noises (Storms, detonations), fear of strangers, excessive howling, damage and destruction in the house. 18 dogs participate in the test and are then followed closely. The device is used every week, the plate impregnated with a new mix of esters of fatty acids. The monitor of the testing makes a first visit to ensure that the behavior problem is such as indicated by the owner. The owner then evaluates the behavior of his dog at the end of each week in terms of improvement, of stability of behavior or deterioration.

Example 3

Administration of Fatty Acid Mixtures to Cats by Diffusion

A mixture of pure esters of fatty acids comprising 35% methyl oleate, 2% dimethyl laurate, 13% methyl stearate, 21% methyl linolate, 5% methyl myristate, 4% methyl pentadecanoate and 20% methyl palmate is prepared. No solvent, vegetable extract of *valeriana* or any other vegetable extract is added to this fatty acid mixture. This solution is placed in a standard device such as an essential oil diffuser (a plate under which one can place a candle) such as shown in FIG. 4 to permit the diffusion of the mixture with the help of heat.

A test is conducted on 22 domestic cats affected by problems of urinary marking. Before inclusion in to this study, the cats undergo a physiological test and behavior history was established. It was also verified that the cats had not received any particular treatment during the two months prior to the test.

In the absence of treatment, the number of urinary marks is counted during a week in order to quantify the problem. The administration of the fatty acid compositions according to the invention is done through diffusion and as per the kinetics previously described. The number of urinary marks is counted during each week of treatment. The treatment is renewed every week, during 4 consecutive weeks.

The invention claimed is:

1. A method of delivering a composition comprising a mixture of pure fatty acids, methyl or ethyl ester derivatives thereof, in a sufficient amount to a non-human mammal by controlled diffusion in the ambient air over a period of at least seven consecutive days with a kinetic of diffusion of 2-3 mg/h during the first three days, about 1.5 to 2 mg/h on the fourth day, about 1 mg/h on the fifth and the sixth days and less than 0.5 mg/h on the seventh day so as to treat symptoms linked to stress or anxiety in said non-human mammal, wherein the said composition does not contain solvent, excipients, vegetable extracts, or even aqueous phase, wherein the controlled diffusion is carried out at a temperature between 100° C. and 140° C., with the proviso that the composition is not an aerosol spray and the controlled diffusion is achieved without addition of any polymer.

2. The method according to claim 1, wherein said composition is pure, non-emulsified or is not dissolved and further does not contain any vegetable extract, vegetable extract of valeriana, and/or aqueous phase.

3. The method according to claim 1, wherein a total of 240 mg of said fatty acids, ester or methyl ester derivatives thereof, are administered to said non-human mammal by diffusion during the seven consecutive days of treatment.

4. The method according to claim 1, wherein said composition comprises a therapeutically effective amount of at least one fatty acid chosen among azelaic acid, pimelic acid, capric acid, lauric acid, myristic acid, palmitic acid, palmitoleic acid, oleic acid, linoleic acid, stearic acid, archidonic acid, n-butyric acid, isobutyric acid, a-methylbutyric acid, caproic acid, pivalic acid, γ-linoleic acid, eicosapentanoic acid, pentadecanoic acid, docosahexenoic acid, or ester or methyl ester derivatives thereof.

5. The method according to claim 4, wherein said composition further comprises a therapeutically effective amount of oleic acid, or ester or methyl ester derivatives thereof.

6. The method according to the claim 5, wherein said composition further comprises a therapeutically effective amount of palmitic acid, or ester or methyl ester derivatives thereof.

7. A method of reducing stress and anxiety of a non-human mammal, of preventing urinary markings, of familiarizing the non-human mammal with a new environment, of preventing stamping or destruction of territory, of noisy outbursts, of dirtiness, of aggressiveness, and/or of reducing recurring idiopathic cystitis, the method comprising administering a therapeutically effective amount of a composition comprising a mixture of pure fatty acids or methyl or ethyl ester derivatives thereof, to the non-human mammal by controlled diffusion with a kinetic of diffusion of 2-3 mg/h during the first three days, about 1.5 to 2 mg/h on the fourth day, about 1 mg/h on the fifth and the sixth days and less than 0.5 mg/h on the seventh day.

8. A kit for reducing the stress and anxiety in a non-human mammal, the kit comprising a composition comprising a mixture of pure fatty acids or methyl or ethyl ester derivatives thereof, wherein the kit administers the mixture to the non-human mammal by controlled diffusion in the ambient air with a kinetic of diffusion of 2-3 mg/h during the first three days, about 1.5 to 2 mg/h on the fourth day, about 1 mg/h on the fifth and the sixth days and less than 0.5 mg/h on the seventh day, the kit further comprising technical instructions.

9. A method of delivering to a non-human mammal a composition comprising a mixture of pure fatty acids, or their methyl or ethyl ester derivatives thereof, wherein the mixture is delivered in a sufficient amount to the non-human mammal by controlled diffusion in the ambient air over a period of at least seven consecutive days with a kinetic of diffusion of,
    (i) higher than about 1.5 mg/h during the first five days, then
    (ii) about 0.5 to 1 mg/h on the sixth day, and then finally
    (iii) less than 0.5 mg/h on the seventh day;
wherein the method is used for treating symptoms linked to stress or anxiety in said non-human mammal, wherein the said composition does not contain solvent, excipients, vegetable extracts, or even aqueous phase, wherein the diffusion is carried out at a temperature between 100° C. and 140° C., with the proviso that the composition is not an aerosol spray and the controlled diffusion is achieved without addition of any polymer.

* * * * *